US012698132B2

(12) United States Patent　　(10) Patent No.:　US 12,698,132 B2

Mitchell　　(45) Date of Patent:　Aug. 4, 2026

(54) FLEXIBLE FRAME FOR USE WITH FLEXIBLE FLUID DISPENSERS

(71) Applicant: Alcon Inc., Fribourg (CH)

(72) Inventor: Jeffrey Thomas Mitchell, Mansfield, TX (US)

(73) Assignee: Alcon Inc., Fribourg (CH)

( * ) Notice: Subject to any disclaimer, the term of this patent is extended or adjusted under 35 U.S.C. 154(b) by 139 days.

(21) Appl. No.: 18/640,135

(22) Filed: Apr. 19, 2024

(65) Prior Publication Data

US 2024/0359871 A1　　Oct. 31, 2024

Related U.S. Application Data

(60) Provisional application No. 63/498,646, filed on Apr. 27, 2023.

(51) Int. Cl.
B65D 35/28　　(2006.01)
A61F 9/00　　(2006.01)

(52) U.S. Cl.
CPC ............ B65D 35/28 (2013.01); A61F 9/0008 (2013.01); A61F 9/0026 (2013.01)

(58) Field of Classification Search
CPC ....... B65D 35/28; A61F 9/0008; A61F 9/0026
See application file for complete search history.

(56) References Cited

U.S. PATENT DOCUMENTS

| | | | | | |
|---|---|---|---|---|---|
| 2,857,079 | A | * | 10/1958 | Hall ....................... | B65D 35/28 |
| | | | | | 222/103 |
| 3,281,016 | A | * | 10/1966 | Thompson ............. | B65D 35/28 |
| | | | | | 222/105 |
| 3,521,807 | A | * | 7/1970 | Weisberg ............. | B65D 77/064 |
| | | | | | 229/117.27 |
| 4,666,064 | A | * | 5/1987 | Hoehn ............... | B65D 47/2037 |
| | | | | | 222/105 |
| 5,074,440 | A | | 12/1991 | Clements | |
| 5,480,066 | A | * | 1/1996 | Blum ..................... | B65D 35/28 |
| | | | | | D9/434 |
| 5,863,562 | A | | 1/1999 | Tsao | |
| 5,890,625 | A | * | 4/1999 | de Laforcade ......... | B65D 35/28 |
| | | | | | 222/103 |

(Continued)

FOREIGN PATENT DOCUMENTS

| | | | |
|---|---|---|---|
| EP | 3738557 | A1 | 11/2020 |
| WO | 2015150002 | A1 | 10/2015 |
| WO | 2020170084 | A1 | 8/2020 |

*Primary Examiner* — Frederick C Nicolas

(74) *Attorney, Agent, or Firm* — Nicholas Smith

(57)　　ABSTRACT

The present disclosure generally relates to a flexible frame for use with a flexible container. The frame includes a first member coupled to a second member at a proximal end. The proximal end is configured to be adjacent to a base of the flexible container when the flexible container is received by the frame. The first and second members are configured to provide additional resistance against displacement of the flexible container by an external compression force to increase purchase and control when using the flexible container. In some embodiments, the frame may also assist in efficiently restoring the shape of the flexible container after the compression force is applied and/or provide feedback regarding the extent of the compressive force applied or contortion experienced by the flexible container.

19 Claims, 10 Drawing Sheets

(56)　　　　　References Cited

U.S. PATENT DOCUMENTS

| | | | | |
|---|---|---|---|---|
| 5,960,993 | A * | 10/1999 | Mitsui | B65D 75/5877 |
| | | | | 222/105 |
| 6,811,057 | B2 * | 11/2004 | Duquet | B65D 75/38 |
| | | | | 222/215 |
| 7,007,831 | B2 * | 3/2006 | Pennaneac'h | A45D 34/04 |
| | | | | 222/215 |
| 7,669,736 | B2 * | 3/2010 | Harper | B65D 75/525 |
| | | | | 222/105 |
| 8,033,428 | B1 * | 10/2011 | McEwin | A47K 1/09 |
| | | | | 222/93 |
| 8,382,010 | B2 | 2/2013 | Nadler | |
| 8,662,350 | B2 * | 3/2014 | Nakatsuka | A61C 5/62 |
| | | | | 222/105 |
| 9,174,777 | B2 | 11/2015 | Defemme | |
| 9,339,375 | B2 | 5/2016 | Lee | |
| 9,402,765 | B2 | 8/2016 | Chibret | |
| 9,463,907 | B2 * | 10/2016 | Barlow | A45D 37/00 |
| 9,833,356 | B2 | 12/2017 | Wochele | |
| 10,538,369 | B2 | 1/2020 | Ritsche | |
| 10,640,268 | B2 | 5/2020 | Painchaud | |
| 10,703,550 | B2 * | 7/2020 | Onesti | B65D 75/525 |
| 11,033,922 | B2 | 6/2021 | Julia | |
| 11,235,914 | B2 | 2/2022 | Pozzi | |
| 11,261,018 | B2 * | 3/2022 | McCutchan | B65D 83/771 |
| 11,319,121 | B2 | 5/2022 | Painchaud | |
| 11,365,031 | B2 | 6/2022 | Pozzi | |
| 11,414,250 | B2 * | 8/2022 | Veit | B65D 75/525 |
| 11,485,548 | B1 * | 11/2022 | Tapocik | A47K 1/09 |
| 11,534,551 | B2 * | 12/2022 | Ferreri | A61M 5/282 |
| 11,633,550 | B2 * | 4/2023 | Fuchs | B05B 11/1011 |
| | | | | 604/294 |
| 11,679,028 | B2 | 6/2023 | Quintana | |
| 2003/0192909 | A1 * | 10/2003 | Maskell | B65D 75/525 |
| | | | | 222/105 |
| 2004/0200860 | A1 | 10/2004 | Buxmann | |
| 2005/0029294 | A1 * | 2/2005 | Jackson | B65D 35/18 |
| | | | | 222/105 |
| 2005/0173459 | A1 | 8/2005 | Buxmann | |
| 2011/0130833 | A1 | 6/2011 | Scott et al. | |
| 2014/0301875 | A1 | 10/2014 | Lee | |
| 2015/0150719 | A1 | 6/2015 | Chibret | |
| 2017/0029175 | A1 | 2/2017 | Decock | |
| 2017/0120272 | A1 | 5/2017 | Decock | |
| 2018/0078455 | A1 | 3/2018 | Defemme | |
| 2018/0078456 | A1 | 3/2018 | Defemme | |
| 2020/0223599 | A1 | 7/2020 | Painchaud | |
| 2020/0262622 | A1 | 8/2020 | Wochele | |
| 2020/0345953 | A1 | 11/2020 | Fuchs | |
| 2021/0322209 | A1 | 10/2021 | Ivri | |

* cited by examiner

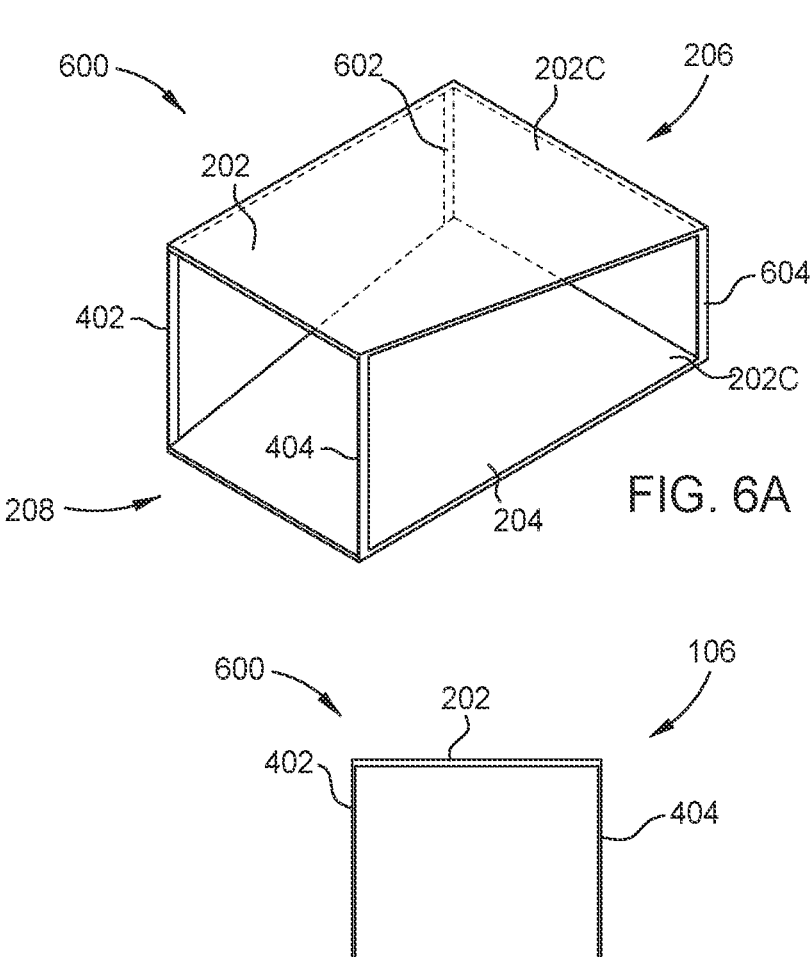
FIG. 6A
FIG. 6B
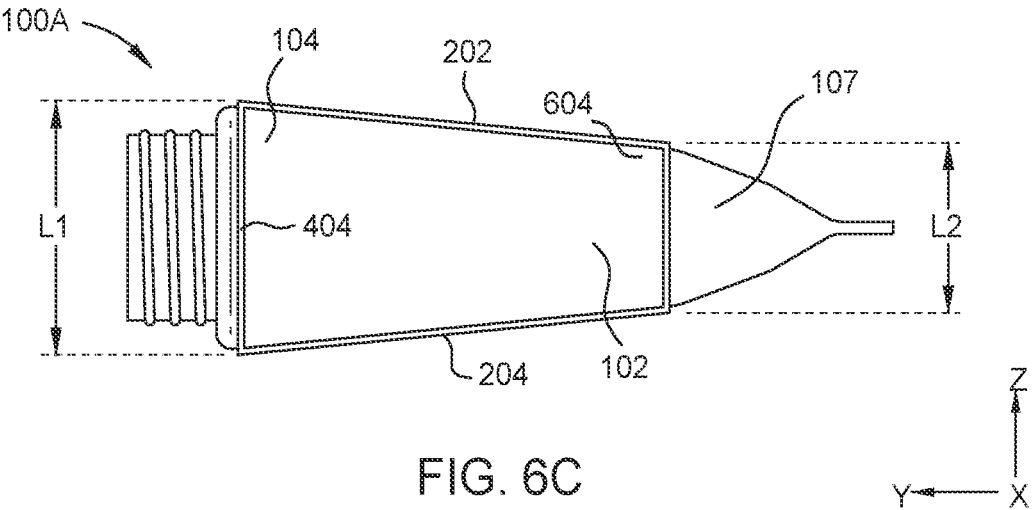
FIG. 6C

FLEXIBLE FRAME FOR USE WITH FLEXIBLE FLUID DISPENSERS

BACKGROUND

Many pathologies of the eye are treated by direct application of fluids to the eye, such as liquid eye drops. For example, conjunctivitis is treated by directly applying eye drops containing antibiotics. Dry eyes and glaucoma are also treated using eye drops. In general, eye drops and other treatment fluids can be used as lubricants for relieving discomfort and dryness of the eyes, as well as delivery vehicles for therapeutic substances.

Eye drops, as well as other treatment fluids, are typically stored in flexible containers. To apply a treatment fluid to a patient's eye, the flexible container is manually compressed by a user to dispense the treatment fluid through a nozzle or other opening in the flexible container. However, it is often difficult to accurately and consistently dispense a desired volume of fluid using such flexible containers. For example, if too much compression force is applied too quickly to the flexible container, an inadvertent over-dispensing or "streaming" of the often limited and costly treatment fluid may occur. Further, where such flexible containers contain multiple doses of fluid for repeated dispensing, variability in compression forces applied to the flexible container between doses may cause variability in dosages of the dispensed treatment fluid.

SUMMARY

Embodiments of the present disclosure generally relate to an apparatus for flexible fluid dispensers, and more specifically, an apparatus for use with flexible containers to improve gripping and control of the dispensing of fluids from the flexible containers.

In certain embodiments, a frame for use with a container is provided. The frame includes a first member coupled to a second member at a proximal end of the frame. The first and second members extend from the proximal end towards a distal end of the frame. The frame is configured to receive the container. When the container is received by the frame, the proximal end of the frame is positioned adjacent to a base of the container and opposite a dispensing end of the container, the first and second members are each in contact with a wall of a body of the container, and the first and second members provide increased resistance against displacement of the external walls of the container by an external compression force.

In other embodiments, a frame for use with a container is provided. The frame includes a first member coupled to a second member at a proximal end of the frame. The first and second members extend from the proximal end towards a distal end of the frame. The frame is configured for use inside the container. When the frame is disposed within the container, the proximal end of the frame is positioned adjacent to a base of the container and opposite a dispensing end of the container, the first and second members are each in contact with an interior surface of a body of the container, and the first and second members provide increased resistance against displacement of the body of the container by an external compression force.

In further embodiments, a frame for use with a container is provided. The frame includes a first spring having a proximal end opposite a distal end, the first spring being curved to form an apex between the proximal end and distal end of the first spring. A first contacting pad is coupled to the apex of the first spring. The frame also includes a second spring having a proximal end opposite a distal end, the second spring being curved to form an apex between the proximal end and distal end of the second spring. The proximal end of the second spring is coupled to the proximal end of the first spring, and a second contacting pad coupled to the apex of the second spring. The frame is configured for use inside the container. When the frame is disposed within the container, the proximal ends of the first and second springs are positioned adjacent to a base of the container opposite a dispensing end of the container, the first and second contacting pads are each in contact with an interior surface of a body of the container, and the first and second springs provide increased resistance against displacement of the body of the container by an external compression force.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIGS. 6A and 6B illustrate a perspective view and a front view, respectively, of yet another flexible frame for use with a flexible container, according to certain embodiments described herein;

FIG. 6C illustrates a side view of the flexible container in FIG. 1A received by the flexible frame in FIGS. 6A and 6B, according to certain embodiments described herein;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the present disclosure provide an apparatus for providing improved control of the dispensing of fluids (including, without limitation, gels, emulsions, suspensions, and the like) from flexible containers. Examples of flexible containers include, without limitation, eye drop dispensers, droptainers, drop bottles, squeeze bottles, dropping bottles, squeeze tubes, and the like. To actuate the dispensing of fluids contained within a flexible container, portions of a body of the flexible container may be compressed or squeezed by a user. This manual compression increases the pressure within the flexible container and/or compresses the fluids therein, thereby causing the fluids to be expelled though an opening of the flexible container, such as a nozzle.

In certain examples, the requisite force needed to dispense fluids from a flexible container may partially depend on the stiffness of the body of the flexible container. For example, the stiffer the body of the flexible container, the greater the amount of compression force necessary to compress the body and dispense fluids therefrom. Conventional flexible containers are typically fabricated from flexible, low-density plastics which enable compression or contortion of such flexible containers with only minimal application of compressive pressure by the user. In some instances, the force applied by a user to merely hold the flexible container can be sufficient to cause dispensing of fluid therefrom. However, the pliability of such plastic materials may lead to fluid being inadvertently dispensed, or an excessive amount of fluid being dispensed, in response to nominal amounts of pressure applied by a user, thereby making accurate and repeatable dispensing of fluids therefrom difficult. Embodiments described herein address these issues.

In certain embodiments, flexible frames for use with flexible containers are provided to assist in improving control over the dispensing of fluids from such flexible containers. In certain embodiments, such flexible frames may function to increase the compression force required to compress or contort the flexible container and dispense fluids therefrom. The flexible frames may also improve the user experience with such flexible containers, such as for example, by assisting in efficiently restoring the shape of the flexible container after compression force is applied, in order to prepare the flexible container for subsequent use. Particular embodiments of the flexible frames may also be configured to enhance user experience by providing feedback to the user regarding the extent of the compressive force applied or contortion experienced by the flexible container. In further embodiments, the flexible frames may also enhance user experience by limiting the flexible container to dispensing predetermined doses with each compression, thereby enabling repeatable and accurate dispensing when using the flexible containers.

Figures 1A, 1B, 1C:
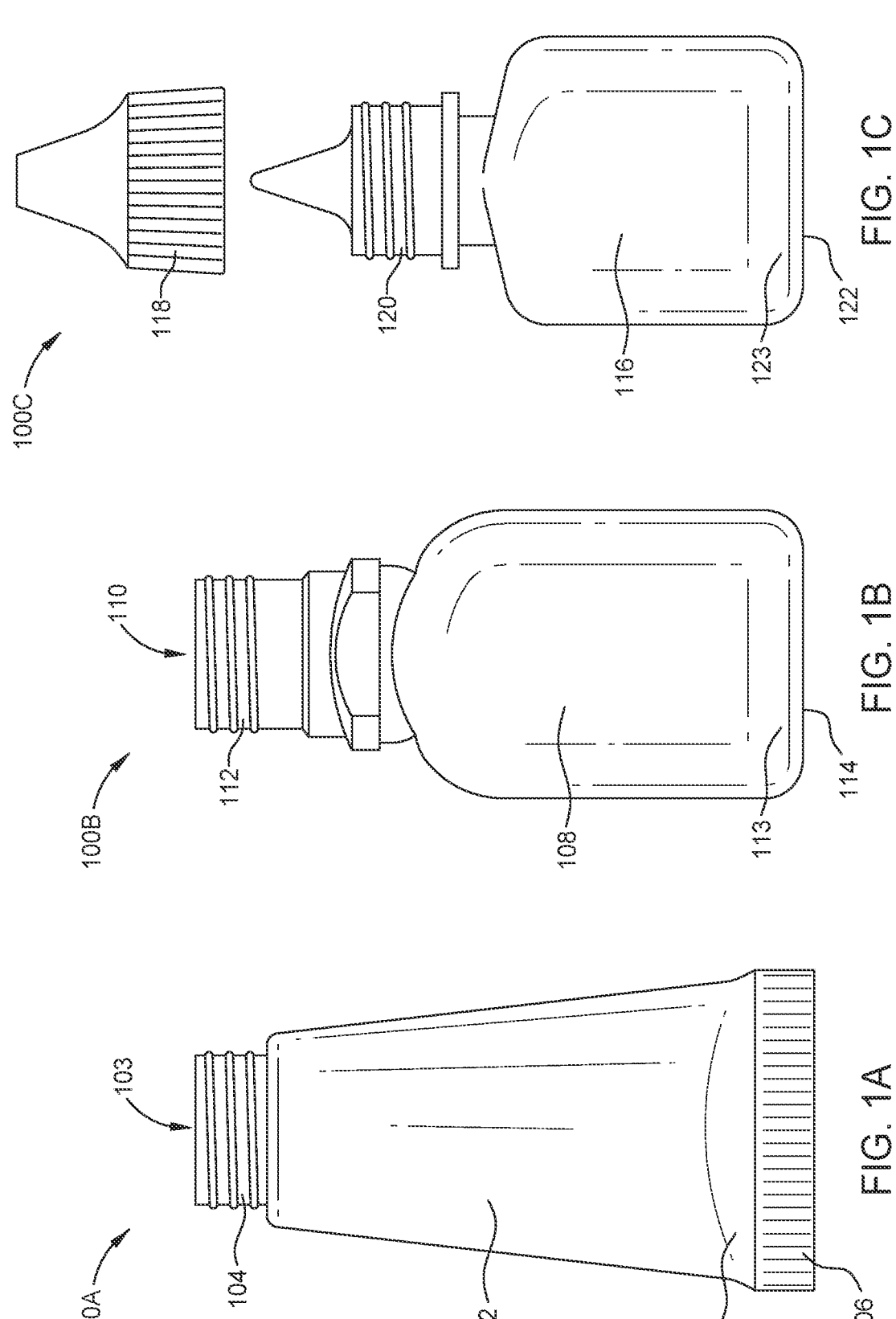
FIGS. 1A-1C illustrate exemplary flexible containers, according to certain embodiments described herein.

FIGS. 1A-1C depict exemplary flexible containers 100A-100C, respectively, that may be used in combination with the flexible frame described herein. FIGS. 1A and 1B depict two flexible containers 100A, 100B showing different examples of bottles or droptainers that may be utilized for dispensing fluids through openings at a dispensing end. FIG. 1C depicts an example flexible container 100C showing another bottle or droptainer that may be utilized for dispensing fluids through a nozzle at a dispensing end. In the description herein, "proximal" with reference to the flexible containers shall be understood as the end of the flexible container comprising a base opposite of the dispensing end of the flexible container. "Distal" with reference to the flexible container shall be understood as the end of the flexible containers from which fluid contained in the flexible containers are dispensed.

In FIG. 1A, the flexible container 100A includes a body 102 having a tapered shape between an opening 103 at a dispensing end 104 and a crimped base 106 at a proximal end 107 of the container 100A. In FIG. 1B, the flexible container 100B includes a tubular body 108 having a cylindrical shape extending between an opening 110 at a dispensing end 112 and a proximal end 113 of the container 100B having an annular base 114. In FIG. 1C, the flexible container 100C includes a tubular body 116 having an ovaloid shape extending between a nozzle 118 at a dispensing end 120 and an annular base 122 at a proximal end 123 of the container 100C. In other embodiments, the flexible containers 100A, 100B may also include nozzles for dispensing fluid from the dispensing ends 104, 112 of the flexible containers 100A, 100B. Fluid from each of the flexible containers 100A, 100B, 100C may be dispensed from an opening/nozzle in the dispensing ends 104, 112, 120 by applying compression forces against the outer surfaces of the bodies 102, 108, 116 of the flexible containers 100A, 100B, 100C, which may then increase the pressure within the flexible containers 100A, 100B, 100C, to force fluids out the opening/nozzle in the dispensing ends 104, 112, 120.

By increasing the compression force required to dispense the contained fluids within each of these exemplary flexible containers 100A, 100B, 100C, particular embodiments of the present disclosure can prevent too much fluid from being dispensed or the fluid from being dispensed too fast due to the flexible containers 100A, 100B, 100C being too easily deformed by the compression force. Particular embodiments of the present disclosure may also assist in addressing difficulties associated with efficient repeated dosing due to delays caused by the flexible containers 100A, 100B, 100C not immediately restoring to their original shapes after the compression force is released. For repeated dosing, embodiments of the present disclosure may also assist in ensuring correct and similar doses are dispensed in each repeated actuations of the flexible containers 100A, 100B, 100C, which may otherwise dispense doses of varying sizes if the compression force applied in each actuation inadvertently varies. Although only three examples of flexible containers are shown in FIGS. 1A to 1C, other flexible containers of varying geometries, shapes, and sizes are also contemplated for use with the various embodiments of the flexible frame discussed below.

Figure 2A:
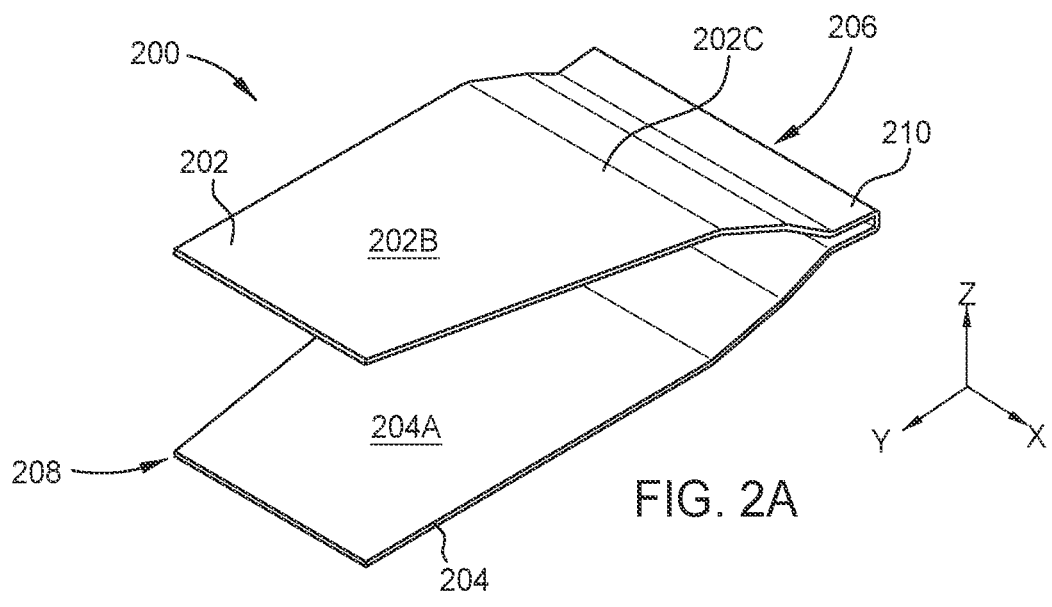
FIGS. 2A and 2B illustrate a perspective view and a side view, respectively, of a flexible frame for use with a flexible container, according to certain embodiments described herein.
Figure 2B:
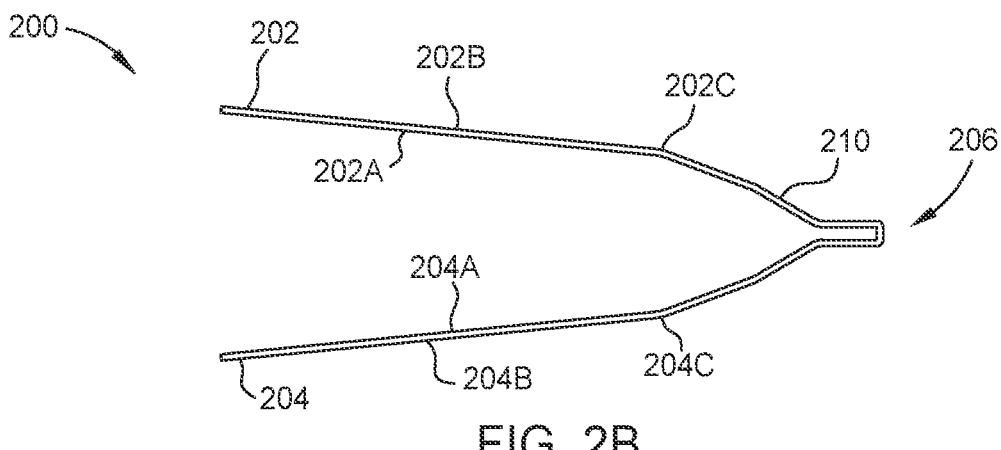
Figure 2C:
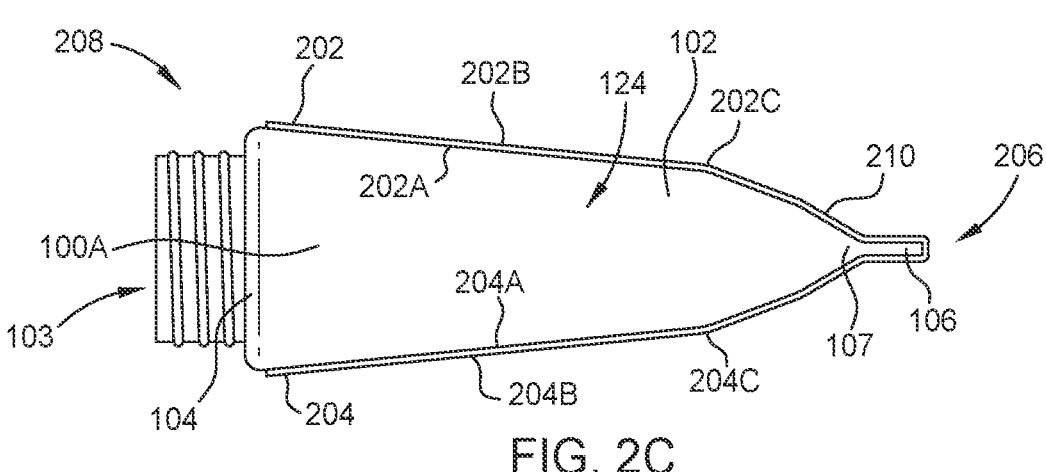
FIG. 2C illustrates a side view of the flexible container in FIG. 1A received by the flexible frame in FIGS. 2A and 2B, according to certain embodiments described herein.

FIGS. 2A-2B show a perspective view and a side view of a flexible frame 200 for use with a flexible container, according to certain embodiments. The embodiments of FIGS. 2A-2B are configured for use with, for example, the flexible container 100A of FIG. 1A. FIG. 2C shows a side view of the flexible container in FIG. 1A received by the flexible frame 200, according to certain embodiments. In some embodiments, the flexible frame 200 may be configured to be coupled to the flexible container 100A along, at least, in part, an exterior surface 124 of the body 102 of the flexible container 100A. However, the flexible frame 200 is only exemplary, and other morphologies, arrangements, and/or configurations of the flexible frame 200 are also contemplated herein for use with flexible containers having other morphologies.

In the description herein, "proximal" with reference to the flexible frame 200 shall be understood as the end of the flexible frame 200 that is closer to a user and generally farther from the dispensing end 104 of the flexible container 100A when the flexible container 100A is received by the flexible frame 200. "Distal" with reference to the flexible frame 200 shall be understood as the end of the flexible frame 200 that is farther from the user and relatively closer to the dispensing end 104 of the flexible container 100A when the flexible frame 200 is coupled to the flexible container 100A.

Turning back to FIGS. 2A and 2B, the flexible frame 200 includes a first member 202 having a first inner surface 202A and a first outer surface 202B opposite of a second member 204 having a second inner surface 204A and a second outer surface 204B. In some embodiments, the first and second members 202, 204 may be formed as mostly planar members which may extend parallel or non-parallel to one another. For example, as shown in FIG. 2A, the first and second members 202, 204 may be planar members coupled at a proximal end 206 and formed to extend non-parallel to one another from the proximal end 206. The first and second members 202, 204 coupled at the proximal end 206 may extend generally in the same distal direction towards a distal end 208 of the flexible frame 200 with the first inner surface 202A of the first member 202 disposed across from and facing the second inner surface 204A of the second member 204.

The first and second members 202, 204 may also be configured to be "mostly" planar with slight curvatures near the distal end 208 due to tubular geometry of the flexible container 100A near the dispensing end 104. In other embodiments, the first and second members 202, 204 may be formed as non-planar members having a curved geometry and configured to correspond with a curved body of a flexible container. For example, the first and second members 202, 204 may be formed with a concave curved profile to match the curved surfaces of the cylindrical tubular bodies 108 and 116 of the flexible containers 100B and 100C shown in FIGS. 1B and 1C.

The flexible frame 200 may be coupled with the flexible container 100A by temporarily moving the first and second members 202, 204 away from each other such that the flexible container 100A may be received between the inner surfaces 202A, 204A of the first and second members 202, 204. When the flexible container 100A is received by the flexible frame 200, the proximal end 206 of the flexible frame 200 may engage with the proximal end 107 of the flexible container 100A, while the inner surfaces 202A, 204A of the first and second members 202, 204 contact the walls of the body 102 of the flexible container 100A. As discussed above, the flexible frame 200 may generally be shaped and sized according to the morphology and dimensions of the body 102 of the flexible container 100A intended for use with the flexible frame 200. The flexible frame 200 may therefore be formed such that when the flexible container 100A is received, the first and second members 202, 204 contact portions of the walls of the body 102 of the flexible container 100A that are typically handled and compressed by a user to dispense fluid from the coupled flexible container 100A.

In some embodiments, the proximal end 206 of the flexible frame 200 comprises a base member 210 extending between a proximal end 202C of the first member 202 and a proximal end 204C of the second member 204. The base member 210 may be configured to match the size and shape of a profile of the crimped base 106 at the proximal end 107 of the flexible container 100A. Matching the base member 210 to the profile of the proximal end 107 of the flexible container 100A enables the proximal end 206 of the flexible frame 200 to snuggly grasp the crimped base 106 and proximal end 107 of the flexible container 100A when the flexible frame 200 is coupled to the flexible container 100A, as shown in FIG. 1C.

In some embodiments, the base member 210 may be formed from the same or different material than the material used to form the first and second members 202, 204, further discussed below. In certain embodiments, the base member 210 may be formed from a stiff material capable of increased traction against or gripping of the proximal end 107 of the flexible container 100A when the flexible frame is coupled to the flexible container. For example, in certain embodiments, the base member 210 may comprise a stiff metallic or thermoplastic polymer material. Examples of stiff metallic materials include aluminum, stainless steel, and other metallic alloys. Examples of stiff thermoplastic polymers include polyetheretherketone (PEEK), polyethylene terephthalate (PET), polycarbonate, nylon, acrylic, and the like. The increased traction or gripping of the proximal end 107 on the flexible container 100A by the base member 210 may assist in holding and/or securing the flexible container 100A within the flexible frame 200 when in use.

In other embodiments, the base member 210 may be formed from a semi-elastic material. The semi-elastic nature of the base member 210 may enable the base member 210 to stretch and conform to the shape of the proximal end 107 of the flexible container 100A when the flexible container 100A is received by the flexible frame 200. In such embodiments, the base member 210 may be sized to have substantially the same dimensions, or slightly smaller dimensions, than the dimensions of the proximal end 107 of the flexible container 100A such that the base member 210 is stretched across the proximal end 107 of the flexible container 100A when coupling the flexible container 100A to the flexible frame 200.

Turning now to FIG. 2C, a side view of the flexible frame 200 from FIGS. 2A and 2B is shown coupled to the flexible container 100A from FIG. 1A. In the example shown, the flexible container 100A may be disposed between the first and second inner surfaces 202A, 204A of the first and second members 202, 204 of the flexible frame 200 and oriented such that the crimped base 106 and proximal end 107 of the flexible container 100A is disposed adjacent to the proximal end 206 of the flexible frame 200, and the opening 103 at the dispensing end 104 of the flexible container 100A is adjacent to the distal end 208 of the flexible frame 200.

In some embodiments, the flexible frame 200 may be sized and shaped based on the size and shape of the flexible container 100A to be used therewith. For example, in certain embodiments, the first and second members 202, 204 may be sized to cover substantially the entire length of the body 102 of the flexible container 100A between the dispensing end 104 and the proximal end 107. Alternatively, the first and second members 202, 204 may be sized to cover only the portions of the flexible container 100A typically compressed by a user when dispensing fluids therefrom. In the example shown in FIG. 2C and as discussed above, the first and second members 202, 204 are formed with a substantially planar geometry to match the opposite planar surfaces of a portion of the body 102 of the flexible container 100A as shown.

The first and second members 202, 204, extending from the proximal end 206 may also extend at angles relative to the base member 210 such that the inner surfaces 202A, 204A substantially match the tapered profile of the body 102 of the flexible container 100A. In certain embodiments, the angle of the first and second members 202, 204 may be formed to maximize contact surface between the inner surfaces 202A, 204A of the first and second members 202, 204 and the exterior surface 124 of the flexible container 100A (in addition to the size and shape). Alternatively, in certain embodiments of the flexible frame 200 such as those formed for use with the flexible containers 100B, 100C shown in FIGS. 1B and 1C, the first and second members 202, 204 may be formed with substantially concave curved profiles due to the rounded cylindrical shape of the bodies 108, 116 of the flexible containers 100B, 100C.

In the example shown in FIG. 2C, when the flexible container 100A is received by the flexible frame 200, the first and second inner surfaces 202A, 204A of the first and second members 202, 204 may contact the external surface 124 of the walls of the body 102 of the flexible container 100A to provide the body 102 with increased resistance against compression force. Generally, the material of the first and second members 202, 204 may be selected based on a material of the flexible container 100A to be received by the flexible frame 200 therewith, the desired amount of resistance to be added to the flexible container 100A in order to counter compressive forces by the user, and the desired amount of additional grip and control to be provided for the user. In certain embodiments, which may be combined with other embodiments herein, the first and second members 202, 204 of the flexible frame 200 are formed of a semi-flexible material having a flexural rigidity (e.g., measured as a Flexural Modulus) greater than the flexural rigidity of the material of the body 102 of the flexible container 100A. For example, the first and second members 202, 204 may be formed of a thermoplastic polymer, a flexible metallic material, and/or combinations thereof. Examples of suitable thermoplastic polymers include high density polyethylene. Examples of suitable metallic materials include nitinol. In certain other embodiments, however, the first and second members 202, 204 may be formed of a semi-flexible material having a similar or lesser flexural rigidity than the material of the body 102. In certain embodiments, the first and second members 202, 204 may be formed of a plastic mono-material or a laminate material.

As mentioned above, when the flexible container 100A is received by the flexible frame 200, the flexible frame 200 may provide the walls of the body 102 of the flexible container 100A in contact with the flexible frame 200 increased resistance and support as compared to when the flexible container 100A is used on its own. This increased resistance and support to the flexible container 100A may therefore increase the amount of applied pressure or compression force required from the user to displace the corresponding walls of the body 102 of the flexible container 100A and dispense fluids from the flexible container 100A. This increase in rigidity or resistance may also prevent the user from inadvertently dispensing fluid from the flexible container 100A when handling the flexible container 100A. In certain examples, the requisite threshold pressure or compressive force to actuate dispensing by the flexible container 100A may be increased by the flexible frame 200 to a level that is typically only applied by the user if applied intentionally, thereby advantageously increasing the likelihood that the flexible container 100A dispenses fluid only in response to intentional forces applied by the user.

In some embodiments, requiring an increased pressure or compressive force by the user to actuate dispensing may also advantageously prevent or reduce the risk of the user applying too much force to the flexible container 100A such that an excessive amount of fluid is dispensed, or that an amount of fluid is dispensed too quickly. For example, the increased resistance or rigidity afforded by the flexible frame 200 may reduce the likelihood that the user over-compresses the flexible container 100A to a point that creates a pressure buildup within the flexible container 20 and forces fluids to be dispensed too quickly, e.g., in the form of a forcible fluidic jet stream.

In some embodiments, the flexible frame 200 may be further configured to limit the amount of displacement of the walls of the body 102 of the flexible container 100A when compressed by a user. For example, in certain embodiments, the flexible frame 200 may be configured to only compress, or displace, the walls of the body 102 a specific distance that corresponds to a desired volume of fluid to be dispensed from the flexible container 100A. In some examples, the desired volume of fluid comprises a desired dose of the treatment fluid being dispensed from the flexible container 100A. Thus, in certain embodiments, the flexible frame 200 is configured to facilitate dispensing of metered doses, by volume, from the flexible container 100A. Accordingly, the flexible frame 200 enables accurate, consistent, and reproducible dispensing of fluids in predetermined doses or aliquots.

In some embodiments, the flexible frame 200 is further configured to provide a restoring force to the flexible container 100A to assist in restoring the flexible container 100A from a compressed state to an uncompressed state after the flexible container 100A is compressed by the user. For example, in certain embodiments, the flexible frame 200 is configured to "spring back," or restore itself, to its original shape after being compressed by the user to actuate a dispensing action from the flexible container 100A. In such embodiments, which may be combined with other embodiments herein, the flexible frame 200 may include an adhesive layer disposed between the inner surfaces 202A, 204A of the first and second members 202, 204 of the flexible frame 200 and the flexible container 100A to adhere the first and second members 202, 204 to the external surface 124 of the flexible container 100A. With the adhesive layer securing the first and second member 202, 204 to the walls of the body 102 of the flexible container 100A, the flexible frame 200 may provide a reliable transfer of energy from the first and second members 202, 204 to the flexible container 100A such that when the flexible frame 200 springs back to its original shape after being compressed, the first and second members 202, 204 adhered to the body 102 also restore the shape of the flexible container 100A. This restoring force provided by the flexible frame 200 may advantageously enable the user to dispense multiple aliquots of fluids from the flexible container 100A in repeated, successive, and distinct dispensing actions.

In further embodiments, which may be combined with other embodiments herein, a separate liner layer may be disposed between the inner surfaces 202A, 204A of the first and second members 202, 204 and the external surface 124 of the flexible container 100A. The additional liner layer may provide increased traction, friction, or grip to assist the flexible frame 200 in holding the flexible container 100A received between the inner surfaces 202A, 204A of the first and second members 202, 204. The additional gripping liner may also be removable from the external surface 124 to allow for the flexible container 100A to be easily removed from the flexible frame 200 for use with another flexible container.

Figure 3A:
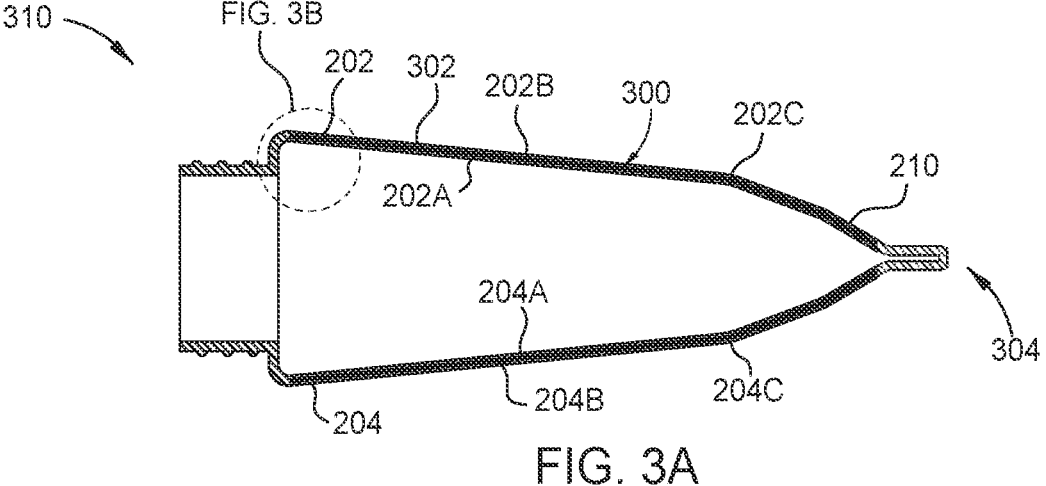
FIG. 3A illustrates a cross-sectional side view of a flexible container fixedly formed with a flexible frame, according to certain embodiments described herein.
Figure 3B:
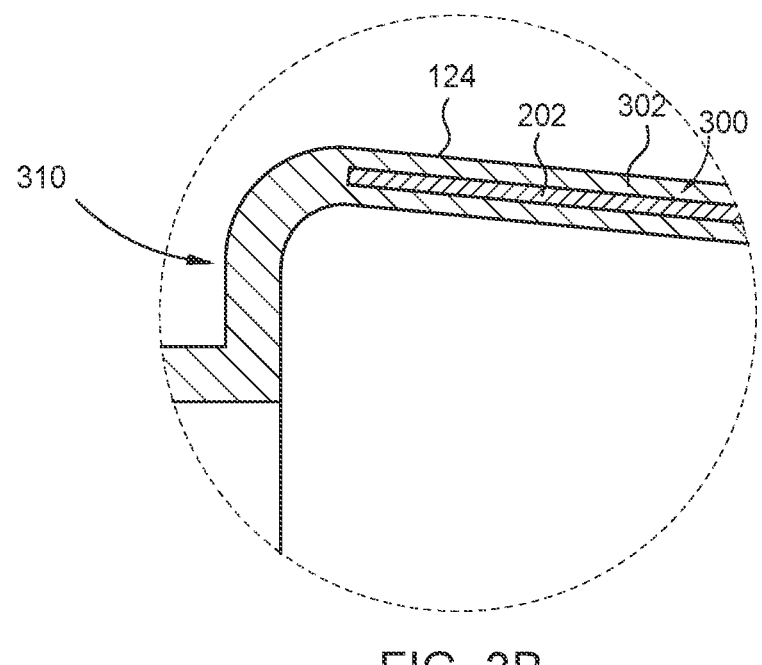
FIG. 3B illustrates an enlarged cross-sectional side view of a portion of the flexible frame in FIG. 3A, according to certain embodiments described herein.

FIGS. 3A and 3B show cross-sectional side views of a flexible container 310 formed with an integrated flexible frame 300, according to certain embodiments. In flexible container 310, the flexible frame 300 may be integrated internally within the walls of a body 302 of the flexible container 310 via, e.g., a co-extrusion process. In certain embodiments, the first and second members 202, 204 of the flexible frame 300 may be optionally coupled at the proximal end 206. If uncoupled, the first and second members 202, 204 may each be separately integrated in portions of the walls of the flexible container 310 opposite from one another. FIG. 3A shows the first and second members 202, 204 separately integrated in the walls of the flexible container 310. Alternatively, if the first and second members 202, 204 are coupled at the proximal end 206, the flexible frame 400 may be integrated within the walls of the body 102 of the flexible container 310 as well as extend through the base of the flexible container 310.

The flexible frame 300 may provide the body 302 of the flexible container 100A with additional resistance against compression force and displacement from within the actual formed portions of the flexible container 310, thereby enabling increased control for a user when dispensing fluids from the flexible container 310. In such examples, the flexible container 310 and the flexible frame 300 may be formed as a single, unitary, and integrated component. Alternatively, the flexible frame 300 may be integrated within the flexible container 310 through an over molding process by injecting the material used for the first and second members 202, 204 into the body 102 of the flexible container 310.

Figure 3C:
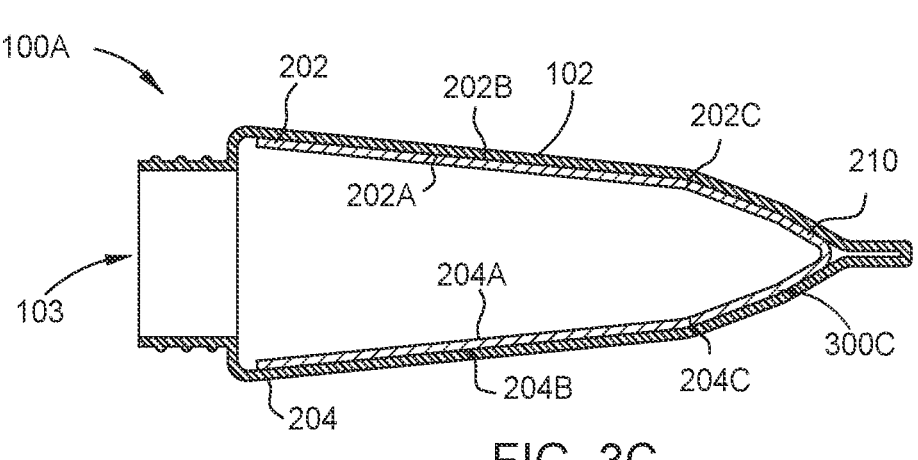
FIG. 3C illustrates a cross-sectional side view of a flexible frame disposed within the flexible container in FIG. 1A, according to certain embodiments described herein.

FIG. 3C shows a cross-sectional side view of an exemplary flexible frame 300C for use within the flexible container 100A in FIG. 1A, according to certain embodiments. In some embodiments, the flexible frame 300C may be configured to be disposed inside the flexible container 100A such that the first and second outer surfaces 202B, 204B of the first and second members 202, 204 are in contact with an interior surface of the body 102 of the flexible frame 100A. In such embodiments, the flexible frame 300C may provide the body 102 of the flexible container 100A with additional resistance against compression force and displacement from inside the flexible container 100A, thereby enabling increased traction and control for a user when dispensing fluids from the flexible container 100A. In such embodiments, the flexible frame 300C may be compressed and inserted within the flexible container 100A through the opening 103 prior to filling the flexible container 100A with fluids.

Figure 4A:
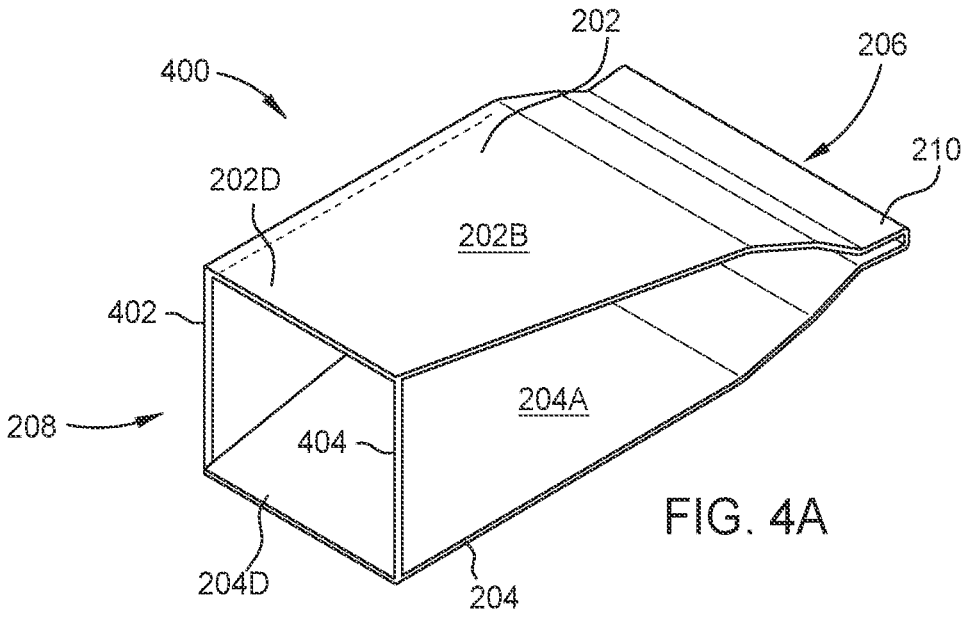
FIG. 4A illustrates a perspective view of another flexible frame for use with a flexible container, according to certain embodiments described herein.

FIG. 4A shows a perspective view of an exemplary flexible frame 400, according to certain embodiments. In such embodiments, in addition to each of the previously described parts of the flexible frame 200, the distal end 208 of the flexible frame 400 may also include a first distal supporting member 402 and a second distal supporting member 404 extending between a distal end 202D of the first member 202 and a distal end 204D of the second member 204. The first and second distal support members 402, 404 may extend between corners of the first and second members 202, 204 directly opposite from one another at the distal end 208 of the flexible frame 400. The first and second distal support members 402, 404, as well as the base member 210, may each be formed of a semi-flexible elastic material configured to be stretched to couple the flexible frame 400 with a flexible container, as well as provide a retracting force to assist in holding the flexible container when received by the flexible frame 400.

Figure 4B:
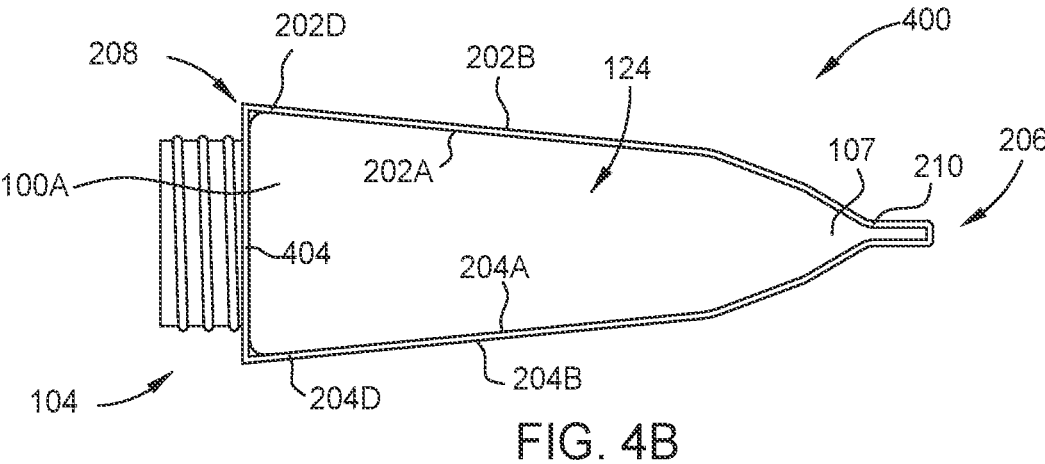
FIG. 4B illustrates a side view of the flexible container in FIG. 1A received by the flexible frame in FIG. 4A, according to certain embodiments described herein.

FIG. 4B shows a side view of the flexible container 100A is received by the flexible frame 400 in FIG. 4A, according to certain embodiments. The first and second distal support members 402, 404 may be configured to stretch and extend across the dispensing end 104 of the flexible container 100A to assist in retaining the flexible container 100A against the base member 210 of the flexible frame 400. The elasticity of the support members 402, 404, may also enable the distance between the inner surfaces 202A, 204A of the first and second members 202, 204 to be varied to allow containers of various sizes to be disposed between the inner surfaces 202A, and 204A for coupling with the flexible frame 400. The first and second distal support members 402, 404 may therefore be sized slightly smaller relative to the dispensing end 104 of the flexible container 100A in the similar manner as the base member 210 is sized relative to the proximal end 107. Further, when a flexible container is received by the flexible frame 400, e.g., the flexible container 100A, the stretching of the first and second distal support members 402, 404 over the dispensing end 104 may assist in retaining the proximal end 107 of the flexible container 100A against the base member 210 of the flexible frame 200. The stretching of the first and second distal support members 402, 404 between the first and second members 202, 204 may also assist in creating a retentive force against the exterior surface 124 of flexible container 100A between the inner surfaces 202A, 204A of the first and second members 202, 204.

Figure 5A:
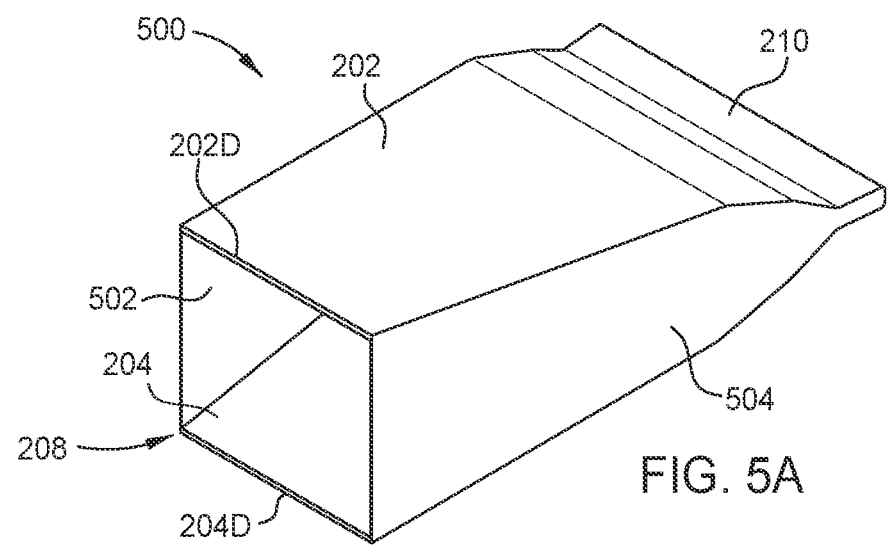
FIG. 5A illustrates a perspective view of yet another flexible frame for use with a flexible container, according to certain embodiments described herein.

FIG. 5A shows a perspective view of an exemplary flexible frame 500, according to certain embodiments. In such embodiments, in addition to each of the previously described parts of the flexible frame 200, the flexible frame 500 may also include a first side member 504 and a second side member 502 extending between the edges on the sides of the first and second members 202, 204. The first side member 502 may extend between the first and second members 202, 204 on one side of the flexible frame 500 and the second side member 504 may extend between the first and second members 202, 204 on the other side. The first and second side members 502, 504 may each be formed of a semi-flexible elastic material similar to the base member 210 and configured to be stretched to provide a retracting/ retaining force when a flexible container is received by the flexible frame 500.

Figure 5B:
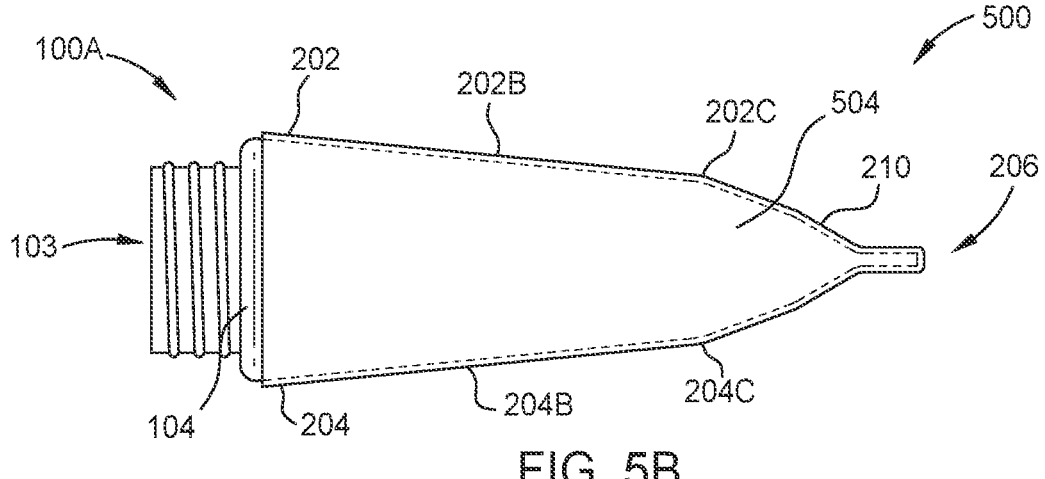
FIGS. 5B and 5C illustrate a side view and a front view, respectively, of the flexible container in FIG. 1A received by the flexible frame in FIG. 5A, according to certain embodiments described herein.
Figure 5C:
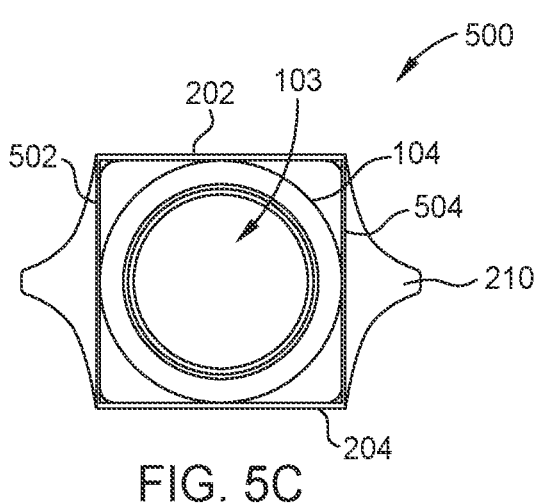

FIGS. 5B and 5C show a side and front view of the flexible container 100A received by the flexible frame 500 in FIG. 5A, respectively, according to certain embodiments. The first and second side members 502, 504 of the flexible frame 500 may be configured to extend across the sides of the body 102 when the flexible container 100A is received by the flexible frame 500. In addition to assisting in retaining the flexible container 100A, the elasticity of the side members 502, 504 may also enable the distance between the inner surfaces 202A, 204A of the first and second members 202, 204 to be varied thereby allowing containers of various sizes to be disposed between the inner surfaces 202A, 204A. In such embodiments, the first and second side members 502, 504 may therefore be sized to have substantially the same dimensions, or slightly smaller dimensions, than the dimensions of the body 102 of the flexible container 100A to allow for the first and second side members 502, 504 to be stretched across the body 102 of the flexible container 100A when the flexible container 100A is received by the flexible frame 500. The flexible frame 500 may therefore provide a retentive force against the exterior surface 124 of flexible container 100A between the inner surfaces 202A, 204A of the first and second members 202, 204 as well as the side members 502, 504.

FIGS. 6A and 6B show a perspective and front view of an exemplary flexible frame 600 for use with the flexible container 100A in FIG. 1A, respectively, according to certain embodiments. In such embodiments, the flexible frame 600 is formed similar to the flexible frame 400 with the exception of the base member 210. At the proximal end 206 of the flexible frame 600, the flexible frame 600 includes a first proximal supporting member 602 and a second proximal supporting member 604 extending between the proximal ends 202C, 204C of the first and second members 202, 204. The first and second proximal support members 602, 604 may extend between corners at the proximal end 102C of the first member 202 and the proximal end 104C of the second member 204 directly opposite from one another at the proximal end 206 of the flexible frame 600. The first and second proximal support members 602, 604 may be formed similar to the first and second distal support members 402, 404 but sized according to the size and shape of the proximal end 107 of the flexible container 100A.

FIG. 6C shows a side view of the flexible container 100A received by the flexible frame 600 in FIGS. 6A and 6B, according to certain embodiments. The first and second proximal support members 602, 604 of the flexible frame 600 may contact and extend laterally around portions of the body 102 of the flexible container 100A near the proximal end 107 of the flexible container 100A. In such embodiments, the base 106 of the flexible container 100A is disposed proximal to the first and second proximal support members 602, 604. The first and second proximal support members 602, 604 may be formed from semi-clastic material similar to the first and second distal support members 402, 404. The stretching of the first and second proximal support members 602, 604 may therefore also assist in creating a retention/gripping force between the first and second members 202, 204 to assist in the coupling of the flexible container 100A with the flexible frame 600.

In certain embodiments, as shown in FIG. 6C, the first and second distal support members 402, 404 may both be formed with a length L1, and the first and second proximal support members 602, 604 may be formed with a length L2. The lengths L1, L2 of the support members 402, 404, 602, 604 may be sized based on the elasticity of the material used for the support members and the required distance between the respective ends 208, 206 of the first and second members 202, 204 perpendicular to a major longitudinal Y axis of the flexible container 100A when received by the flexible frame 600. In the examples shown, L1 may therefore be formed longer than L2 due to the tapering geometry of the flexible container 100A between the dispensing end 104 and the proximal end 107 of the flexible container 100A. In other embodiments, such as when the flexible frames 600 is configured to receive the flexible container 100B in FIG. 1B where the geometry of the body 108 is substantially consistent between the dispensing end 112 and the proximal end 113, L1 of the first and second distal support members 402, 404 and L2 of the first and second proximal support members 602, 604 may be substantially the same.

As mentioned above, the first and second distal support members 402, 404 and the first and second proximal support members 602, 604 may be formed from a semi-clastic flexible material capable of being stretched to facilitate coupling of the flexible container 100A between the inner surfaces 202A, 204A of the first and second members 202, 204. In such embodiments, the elastic material may enable the supporting member 402, 404, 602, 604 to accommodate respective portions of flexible containers having different dimensions and sizes. The elasticity of the support members 402, 404, 602, 604 enables the distance between the first and second members 202, 204 to be varied, thereby allowing the flexible frame 600 to receive flexible containers of various sizes. Further, when the flexible frame 600 is engaged with a flexible container, e.g., the flexible container 600, the support members 402, 404, 602, 60, retain the flexible container 100A within the flexible frame 600 by creating a lateral retentive force against the exterior surface 124 of flexible container 100A between the first and second members 202, 204.

Figure 7A:
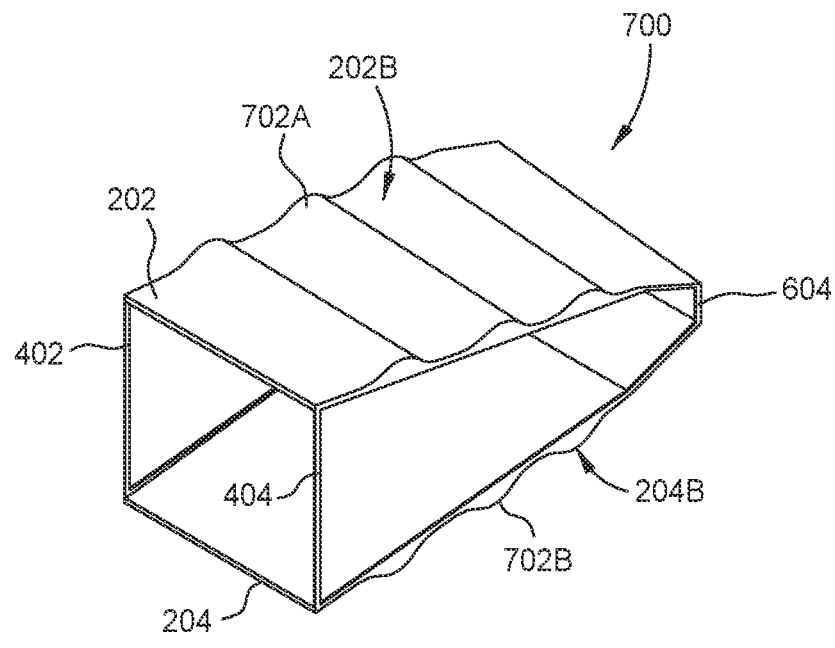
FIG. 7A illustrates a perspective of yet another flexible frame having a gripping feature, according to certain embodiments described herein.
Figure 7B:
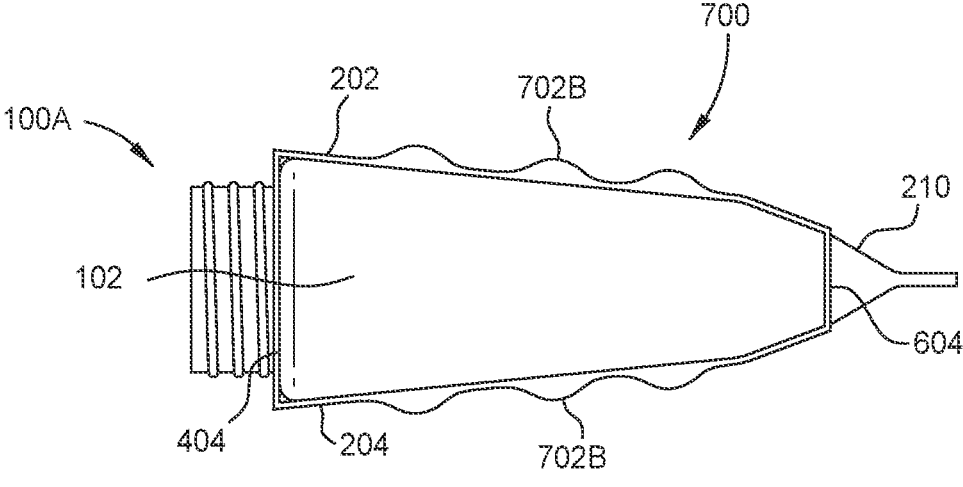
FIG. 7B illustrates a cross-sectional side view of the flexible container in FIG. 1A received by the flexible frame in FIG. 7A, according to certain embodiments described herein.

FIG. 7A shows an exemplary flexible frame 700 for use with a flexible container, according to certain embodiments. FIG. 7B shows a side view of the flexible container 100A received by the flexible frame 700 in FIG. 7A, according to certain embodiments. Flexible frame 700 may be formed substantially similar to any one of the flexible frames 200, 400, 500, and 600 described above. In certain embodiments, which may be combined with other embodiments herein, flexible frame 700 includes gripping features 702A, 702B formed in the first and second members 202, 204.

The gripping features 702A, 702B may be used to assist in the handling and control of the flexible container 100A when received by the flexible frame 700. As shown in FIG. 7A, the gripping features 702A, 702B may include grooves formed in the first and second outer surfaces 202B, 204B and configured to be held by the user. However, other features, such as ridges, bumps, and the like, are also contemplated. Additionally, or alternatively, the gripping features 702A, 702B may include, without limitation, a textured or patterned surface, contoured shapes and lines, and/or any other three-dimensional geometries formed in one or more of the first and second outer surfaces 202B, 204B of the first and second members 202, 204.

Figure 8A:
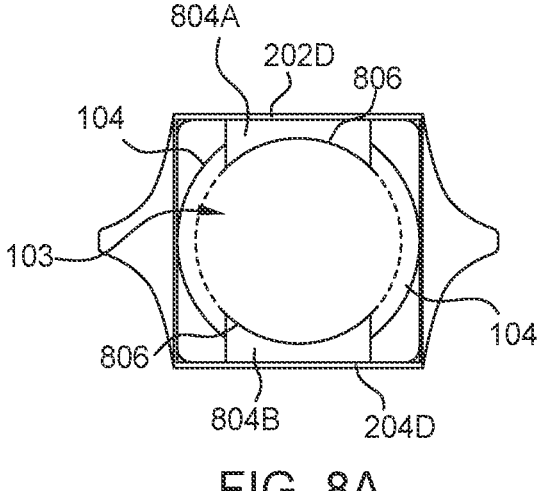
FIG. 8A illustrates a front view of yet another flexible frame having a locking feature, according to certain embodiments described herein.
Figure 8B:
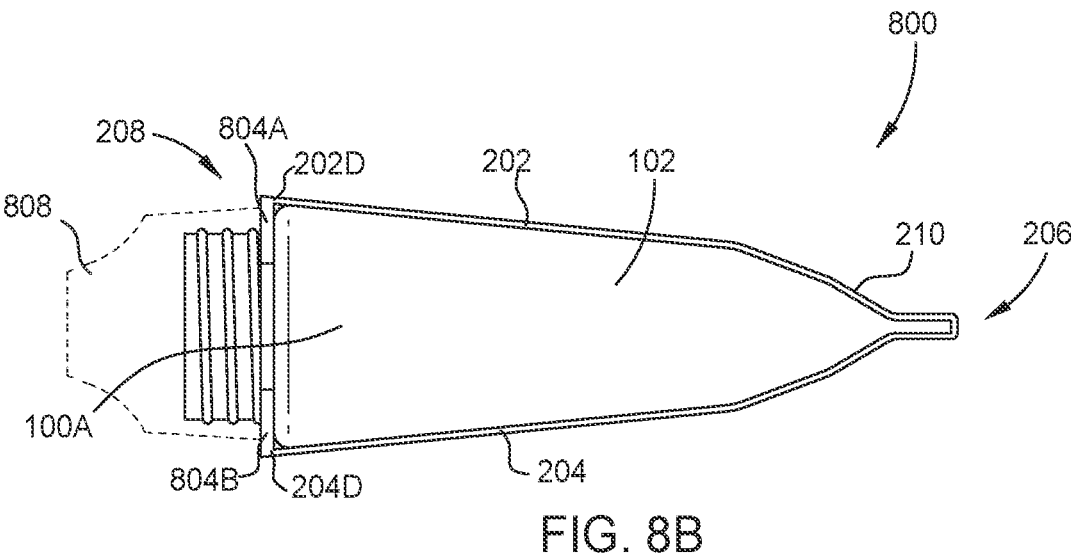
FIG. 8B illustrates a cross-sectional side view of the flexible container in FIG. 1A received by the flexible frame in FIG. 8A, according to certain embodiments described herein.

FIGS. 8A and 8B show a front view and a side view of an exemplary flexible frame 800 used with the flexible container 100A depicted in FIG. 1A, according to certain embodiments. The flexible frame 800 may include a locking mechanism configured to minimize the displacement of the walls of the body 102 (and thus, fluid from being dispensed therefrom) when the flexible container 100A is not in use and a cap 808 is affixed over the opening 103 of the flexible container 100A. The locking mechanism may include first and second locking members 804A, 804B formed at the distal end 208 of the flexible frame 800 and configured to interact with the dispensing end 104 of the flexible container 100A when the cap 808 is affixed over the opening 103. In some embodiments, the locking members 804A, 804B may extend from the distal ends 202D, 204D of the first and second members 202, 204. In other embodiments, the locking members 804A, 804B may extend from the first and second distal support members 402, 404 of the flexible frame 800, if present. In the example shown in FIG. 8B, the locking members 804A, 804B extend from the distal ends 202D, 204D, of the first and second members 202, 204 towards the opening 103 when the flexible container 100A is received by the flexible frame 800.

The first and second locking members 804A, 804B may each include one or more surfaces 806 configured to interact with the cap 808 when the cap 808 is affixed over the opening 103 of the flexible container 100A. The surfaces 806 of the first and second locking members 804A, 804B may each contact and mate with corresponding opposite portions of the exterior surface of the cap 808 disposed over the opening 103 between the first and second locking members 804A, 804B. The engagement of the first and second locking members 804A, 804B with the cap 808 may therefore operate as a lock and block the distal ends 202D, 204D of the first and second members 202, 204 from moving towards one another, thereby creating additional resistance to protect the flexible container 100A from compression force. The flexible container 100A received by the flexible frame 800 may therefore reduce the chances of accidental actuation of the dispensing action through contact by a compression force when the cap 808 is secured over the opening 103.

In other embodiments, as shown in FIG. 8B, the locking members 804A, 804B may also be configured such that the interaction between the locking members 804A, 804B and the cap 810 when the cap 810 is secured over the opening 103 of the flexible container 100A may cause the flexible frame 800 to hold and maintain the flexible container 100A in its original shape to reduce the possibility of an accidental actuation of the flexible container 100A when not in use. When the cap 808 is not in use, a gap corresponding to the position of the cap 808 around the opening 103 is formed between the locking members 304A, 304B and the opening 103. When the cap 808 is removed from the opening 103, the gap allows for the flexible frame 800 to be used and the first and second members 202, 204 to be compressed normally without interference from the locking members 804, 804B.

In further embodiments, when the cap 808 is installed on the flexible container 100A, the locking members 804A, 804B may alternatively push the flexible frame 800 to a further expanded position such that the distance between the distal ends 202D, 204D of the first and second members 202, 204 is increased. In certain embodiments where the exterior surface 124 of the flexible container 100A is adhered to the inner surfaces 202A, 204A of the first and second members 202,204, increasing the distance between the first and second members 202, 204 may correspondingly cause the pressure inside the flexible container 100A to decrease after fluid is dispensed from the flexible container 100A and the cap 808 is installed. In further embodiments, which may be combined with other embodiments herein, the locking members 804A, 304B may lock the flexible frame 800 in an expanded position such that any force applied against the first and second members 202, 204 may be dampened by the increased distance between the distal ends 202D, 204D of the first and second members 202, 204.

Figure 9A:
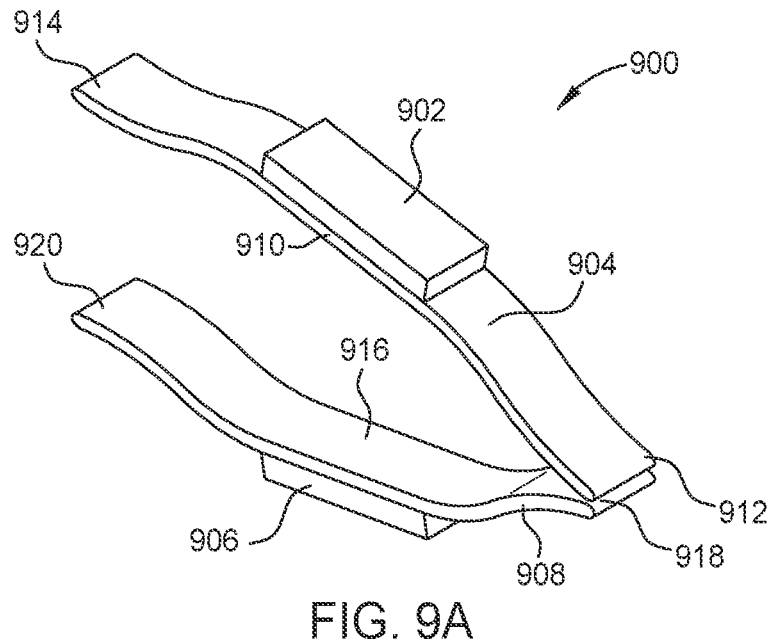
FIG. 9A illustrates a perspective view of yet another flexible frame for use with a flexible container, according to certain embodiments described herein.

FIG. 9A shows a perspective view of an exemplary flexible frame 900, according to certain embodiments. Similar to the flexible frame 300C in FIG. 3C, flexible frame 900 is configured to provide the walls of the body 102 with support and resistance from inside the flexible container 100A, according to certain embodiments. The flexible frame 900 includes a first contacting pad 902 coupled to a first spring 904, and a second contacting pad 906 coupled to a second spring 908. The flexible frame 900 may be disposed inside the flexible container 100A to provide the walls of the body 102 of the flexible container 100A with additional resistance against compression forces.

In certain embodiments, the first and second springs 904, 908 may be flat springs having rectangular cross-sections each formed in the shape of an arc. The first spring 904 includes an apex 910 at the peak of the arc between a proximal end 912 and a distal end 914. The second spring 908 includes an apex 916 at the peak of its arc between a proximal end 918 and a distal end 920. Due to the curvature in the shape of the first and second springs 904, 908, each of the springs 904, 908 are configured to deflect or resist against forces applied on the apexes 910, 916 of the springs 904, 908. The first contacting pad 902 may be coupled to the first spring 904 at the apex 910, and the second contacting pad 906 may be coupled to the second spring 908 at the apex 916. The proximal end 912 of the first spring 904 may be coupled to the proximal end 918 of the second spring 908. The flexible frame 900 may be configured to be compressible for insertion into the flexible container 100A through opening 103 at the dispensing end 104 of the flexible container 100A. When the frame 900 is disposed inside the flexible container 100A, the frame 900 may expand inside the flexible container 100A and contact an interior surface of the body 102 of the flexible container 100A.

Figure 9B:
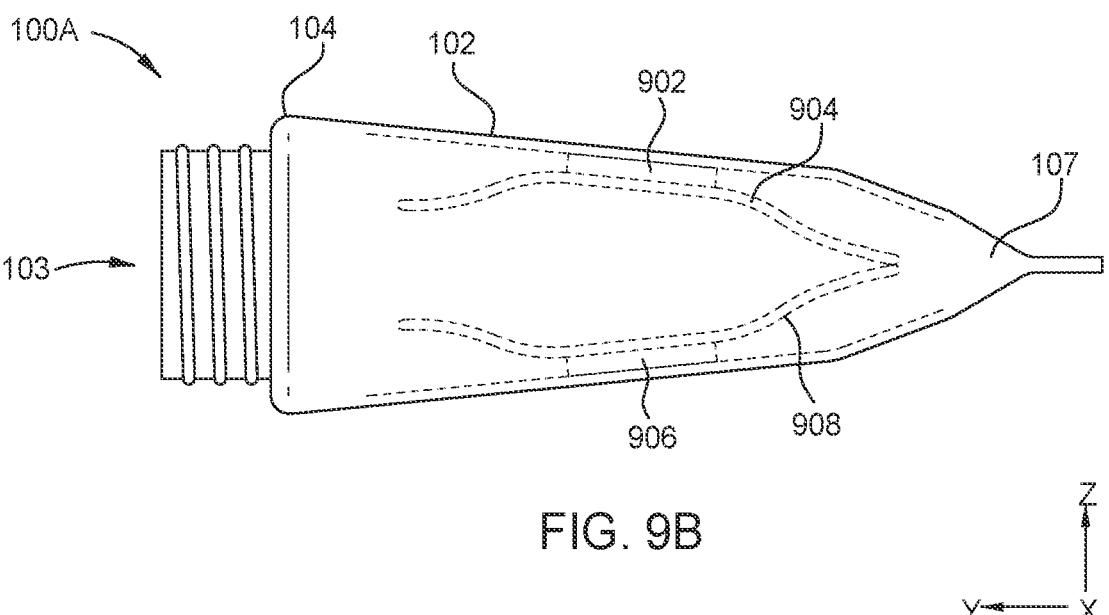
FIG. 9B illustrates a side view of the flexible frame in FIG. 9A shown in phantom lines and disposed within the flexible container in FIG. 1A, according to certain embodiments described herein.

FIG. 9B shows a side view of the flexible frame 900 in FIG. 9A disposed with the flexible container 100A depicted in FIG. 1A, according to certain embodiments. When the frame 900 is inside the flexible container 100A, the first and second contacting members 902, 906 may be positioned opposite of one another in contact with the interior surface of the body 102 of the flexible container 100A. The first spring 904 coupled to the first contact pad 902 may extend along the longitudinal Y axis of the flexible container 100A with the proximal end 912 of the first spring 904 disposed towards the proximal end 107 of the flexible container 100A. The distal end 914 of the first spring 904 may therefore extend towards the dispensing end 104 of the flexible container 100A and be disposed against the interior surface of the body 102 near the opening 103 of the flexible container 100A. The second spring 908, coupled to the first spring 904 at the proximal end 918, may correspondingly be disposed inside the flexible container 100A with the proximal end 918 of the second spring 908 disposed towards the proximal end 107 of the flexible container 100A and the distal end 920 disposed against the interior surface of the body 102 near the opening 103 of the flexible container 100A.

When the first and second springs 904, 908 are disposed inside the flexible container 100A, the springs 904, 908 may deflect in response to a compression force applied to the body 102 of the flexible container 100A due to the contact between the first and second contacting pads 902, 906 and the interior surfaces of the flexible container 100A. When a compression force is applied against the first and second contacting pads 902, 906, and hence, the apexes 910, 916, of the first and second springs 904, 908, respectively, the first and second springs 904, 908 may in turn deflect against the compression force thereby providing the walls of the flexible container 100A with additional resistance against the compression force. When the first and second springs 904, 908 deflect, the proximal ends 912, 918, may bank against one another and the distal ends 914, 920 may bank against opposite interior surfaces of the flexible container 100A when the first and second springs 904, 908.

The first and second springs 904, 908 coupled to the first and second contacting pads 902, 906 may therefore support the first and second contacting pads 902, 906 against the interior surface of the flexible container 100A and enable the contacting pads 902, 906 to provide a resistive force directed outwards against the walls of the body 102. The resistive deflecting force from the springs 904, 908 in turn may similarly also increase the force and pressure necessary to be applied by the user to the exterior surface 124 of the flexible container 100A to actuate and dispense fluids from the flexible container 100A.

Figure 10:
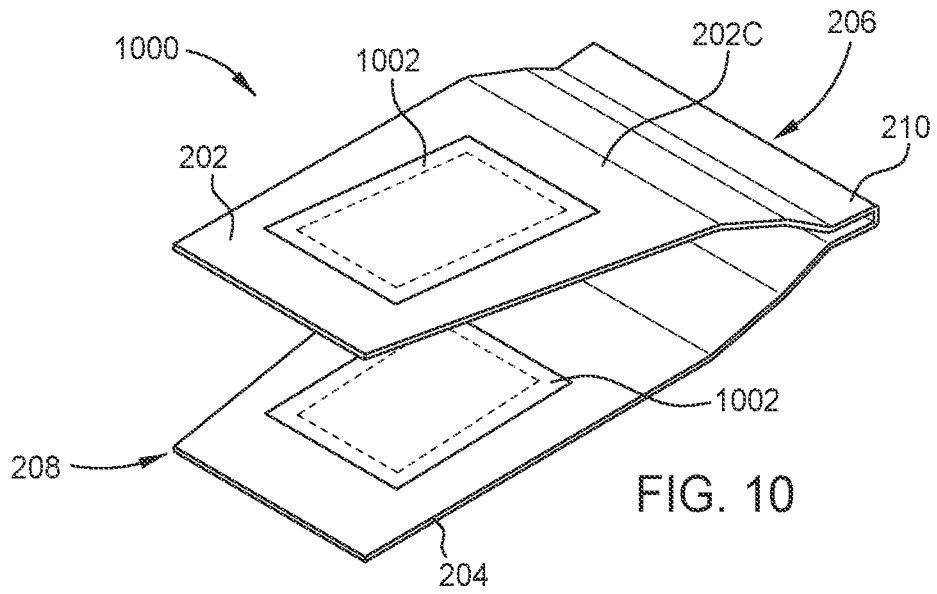
FIG. 10 illustrates a perspective view of yet another flexible frame having a feedback feature, according to certain embodiments described herein.

FIG. 10 shows a perspective view of an exemplary flexible frame 1000, according to certain embodiments. The flexible frame 1000 includes a feedback mechanism configured to indicate to the user the occurrence of certain events with respect to the flexible container 100A when used by the user. For example, the feedback mechanism may provide feedback to the user when the flexible frame 1000 is manipulated to actuate and dispense fluid from a flexible container received by the flexible frame 1000, e.g., the flexible container 100A received therewith. In certain embodiments, the feedback may be provided when a specific force has been applied by the user to the flexible frame 1000 in the dispensing action, a specific displacement or deformation in the flexible frame 1000 occurs, or a combination of both when a specific force is applied and when a specific displacement occurs in the flexible frame 1000. The feedback may be configured based on when a dose of the fluid within the flexible container 100A should have been administered based on either the specific force applied by the user and/or the specific displacement of the flexible frame 1000 in contact with the flexible container 100A having occurred. In certain embodiments, the feedback from the feedback mechanism may be in the form of haptic feedback to be physically felt by the user when handling the flexible frame 1000. In other embodiments, the feedback may be in the form of audible feedback to be heard by the user Turning now to FIG. 10, in certain embodiments, the feedback mechanism for the first and second members 202, 204 comprises a blistable spring member 1002. The blistable spring member 1002 may be manipulated between two stable states and "snap" when a specific force is applied during such manipulation. Incorporating the blistable spring member 1002 into the first and second members 202, 204 enables the blistable spring member 1002 to be contacted directly by the user when the flexible frame 1000 is manipulated to actuate the dispensing action from the flexible container. Such "snapping" of the blistable spring member 1002 when the first and second members 202, 204 are compressed may therefore be utilized to provide the aforementioned haptic feedback, audible feedback, or both.

Figure 11:
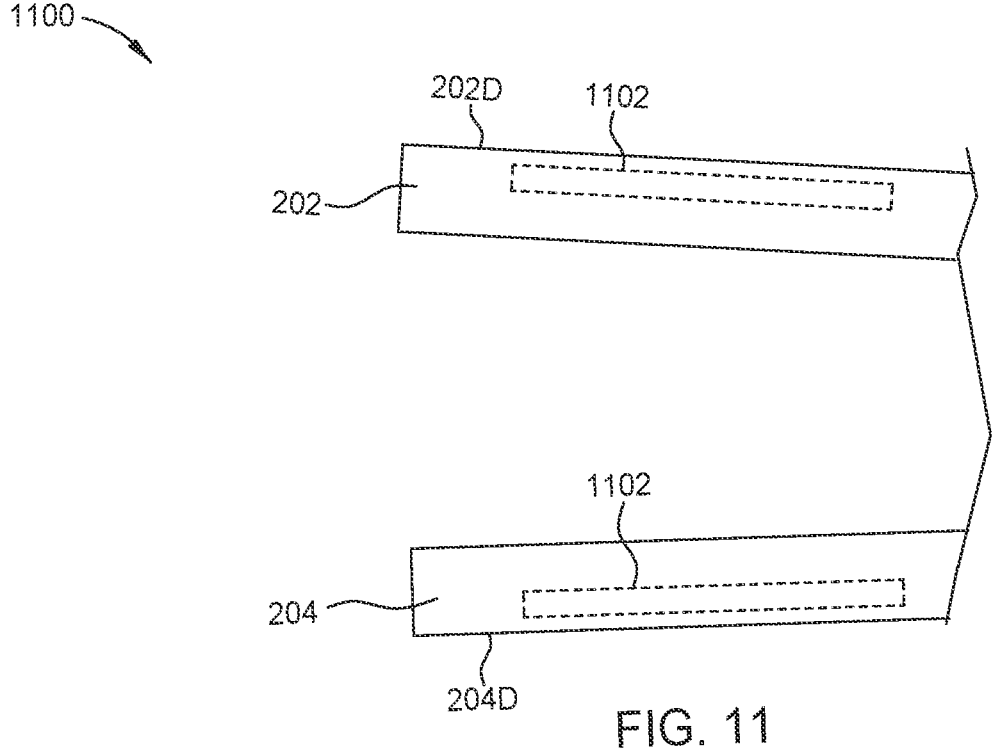
FIG. 11 illustrates an enlarged side view of a portion of a flexible frame having a feedback feature, according to certain embodiments described herein.

FIG. 11 shows a side view of a portion of an exemplary flexible frame 1100 comprising a feedback mechanism, according to certain embodiments. The feedback mechanism comprises one or more air pockets 1102 formed in the walls of each of first and second members 202, 204. The air pockets 1102 may be disposed in the first and second members 202, 204 adjacent to respective outer surfaces 202B, 204B of the first and second members 202, 204. In such embodiments, the walls of the first and second members 202, 204 may be configured to bend and "snap" into the respective air pocket 1102 upon application of a specific compressive force against the outer surfaces 202B, 204B by a user. The "snapping" of the one or more air pockets 1102 in the walls of the first and second members 202, 204 may provide haptic feedback, audible feedback, or both haptic and audible feedback, to the user, thereby signifying to the user that the flexible container received by the flexible frame 1100 therewith has been compressed a certain distance (and thus, a certain volume of fluids has been dispensed therefrom). Although depicted in FIGS. 10 and 11 with flexible frames 1000, 1100 configured to receive flexible containers, the feedback mechanisms described herein may be used in combination with flexible frames configured to be disposed within flexible containers as well.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A frame for use with a container, comprising:
   a first member;
   a second member coupled to the first member at a proximal end of the frame opposite a distal end of the frame, the first and second members both extending from the proximal end towards the distal end;
   wherein the frame is configured to receive the container; and
   wherein when the container is received by the frame:
      the proximal end of the frame is positioned adjacent to a base of the container opposite a dispensing end of the container;
      the first and second members are each in contact with a wall of a body of the container;
      the first and second members provide increased resistance against displacement of external walls of the container by an external compression force; and
      the frame further comprises a liner layer between the container and the first and second members, and wherein the liner layer provides traction, friction, or grip between the container and each of the first and second members.

2. The frame of claim 1, wherein when the container is received by the frame, the coupling of the first and second members at the proximal end of the frame comprises one or more flexible support members extending between the first and second members, wherein the one or more flexible support members are configured to provide a retention force between the first and second members at a proximal end of the container.

3. The frame of claim 1, wherein when the container is received by the frame, the distal end of the frame further comprises one or more flexible support members extending between the first and second members, and wherein the one or more flexible support members are configured to provide a retention force between the first and second members at a distal end of the container.

4. The frame of claim 1, wherein the first and second members comprise a plastic mono-material, a laminate material, a thermoplastic polymer, high density polyethylene, a flexible metallic material, nitinol, and/or combinations thereof.

5. The frame of claim 1, wherein when the container is received by the frame, the frame further comprises an adhesive between the container and the first and second members.

6. The frame of claim 1, wherein when the container is received by the frame, the first and second members comprise a semi-flexible material having a flexural rigidity greater than the flexural rigidity of a body of the container.

7. The frame of claim 1, wherein when the container is received by the frame, the first and second members are configured to provide a restoring force to the container, wherein the restoring force assists in restoring the container from a compressed state to an original state after the container is contorted to the compressed state by the external compression force.

8. The frame of claim 1, wherein at least one of the first and second members further comprises a gripping feature to assist in handling the frame.

9. The frame of claim 1, wherein when the container is received by the frame, the first and second members are configured to limit the displacement of the container when the external compression force is applied to the container through the frame.

10. A frame for use with a container, comprising:
a first member;
a second member coupled to the first member at a proximal end of the frame opposite a distal end of the frame, the first and second members both extending from the proximal end towards the distal end;
a locking feature at the distal end of the frame;
wherein the frame is configured to receive the container;
wherein the locking feature is configured to interact with a cap affixed over an opening at a dispensing end of the container; and
wherein when the container is received by the frame:
the proximal end of the frame is positioned adjacent to a base of the container opposite a dispensing end of the container;
the first and second members are each in contact with a wall of a body of the container;
the first and second members provide increased resistance against displacement of external walls of the container by an external compression force; and
the locking feature is configured to hold and maintain the container in an uncompressed state when the cap is affixed over the opening of the container.

11. The frame of claim 10, wherein the locking feature comprises a first locking member extending from the first member and a second locking member extending from the second member, and wherein when the container is received by the frame, the first and second locking members are configured to interact with the cap when the cap is affixed over the opening of the container.

12. The frame of claim 10, wherein when the container is received by the frame, the coupling of the first and second members at the proximal end of the frame comprises one or more flexible support members extending between the first and second members, wherein the one or more flexible support members are configured to provide a retention force between the first and second members at a proximal end of the container.

13. The frame of claim 10, wherein when the container is received by the frame, the distal end of the frame further comprises one or more flexible support members extending between the first and second members, and wherein the one or more flexible support members are configured to provide a retention force between the first and second members at a distal end of the container.

14. The frame of claim 10, wherein when the container is received by the frame, the first and second members are configured to provide a restoring force to the container, wherein the restoring force assists in restoring the container from a compressed state to an original state after the container is contorted to the compressed state by an external compression force.

15. A frame for use with a container, comprising:
a first member;
a second member coupled to the first member at a proximal end of the frame opposite a distal end of the frame, the first and second members both extending from the proximal end towards the distal end;
wherein the frame is configured to receive the container; and
wherein when the container is received by the frame:
the proximal end of the frame is positioned adjacent to a base of the container opposite a dispensing end of the container;
the first and second members are each in contact with a wall of a body of the container;
the first and second members provide increased resistance against displacement of external walls of the container by an external compression force; and
at least one of the first and second members further comprises a feedback feature configured to provide a feedback in response to when a specific external compression force is applied to the at least one of the first and second members, when the specific external compression force causes a specific displacement or deformation in the container to occur, or both.

16. The frame of claim 15, wherein the feedback by the feedback feature comprises an audible and/or a haptic feedback provided by the at least one of the first and second members.

17. The frame of claim 15, wherein when the container is received by the frame, the coupling of the first and second members at the proximal end of the frame comprises one or more flexible support members extending between the first and second members, wherein the one or more flexible support members are configured to provide a retention force between the first and second members at a proximal end of the container.

18. The frame of claim 15, wherein when the container is received by the frame, the distal end of the frame further comprises one or more flexible support members extending between the first and second members, and wherein the one or more flexible support members are configured to provide a retention force between the first and second members at a distal end of the container.

19. The frame of claim 15, wherein when the container is received by the frame, the first and second members are configured to provide a restoring force to the container, wherein the restoring force assists in restoring the container from a compressed state to an original state after the container is contorted to the compressed state by an external compression force.

\* \* \* \* \*